United States Patent [19]

Rasmussen et al.

[11] Patent Number: 5,520,762
[45] Date of Patent: May 28, 1996

[54] METHOD OF MANUFUCTURING A WOUND DRESSING DELIVERY SYSTEM

[75] Inventors: Mark J. Rasmussen, Forney; Tod H. Shultz, Arlington; Michael B. Killeen, Jr., Coppell, all of Tex.

[73] Assignee: Wilshire Technologies, Inc. (Wilshire Medical Products Division), Dallas, Tex.

[21] Appl. No.: 173,638

[22] Filed: Dec. 23, 1993

[51] Int. Cl.⁶ .................................................. B32B 31/00
[52] U.S. Cl. .................. 156/216; 156/242; 156/289; 156/331.7; 156/332; 156/267; 156/256; 602/57; 602/42; 602/56; 206/441
[58] Field of Search .................................. 156/289, 230, 156/249, 242, 216, 331.7, 332, 267, 256; 602/41, 42, 52, 56, 57, 58; 206/440, 441

[56] References Cited

U.S. PATENT DOCUMENTS

| | | | |
|---|---|---|---|
| 2,969,057 | 1/1961 | Simmons | 128/2 |
| 3,349,765 | 10/1931 | Blanford | 128/132 |
| 3,425,412 | 2/1969 | Pope | 128/156 |
| 4,324,237 | 4/1982 | Buttaravoli | 128/214 |
| 4,485,809 | 12/1984 | Dellas | 128/156 |
| 4,570,627 | 2/1986 | MacConkey et al. | 128/132 |
| 4,646,731 | 3/1987 | Brower | 128/156 |
| 4,650,705 | 3/1987 | Ghodsian | 428/40 |
| 4,744,355 | 5/1988 | Faasse, Jr. | 128/156 |
| 4,747,401 | 5/1988 | Porter et al. | 128/156 |
| 4,807,613 | 2/1989 | Koehnke et al. | 128/155 |
| 4,837,062 | 6/1989 | Dunshee et al. | 428/41 |
| 4,915,102 | 4/1990 | Kwiatek et al. | 128/156 |
| 4,917,112 | 4/1990 | Kalt | 128/156 |
| 4,926,850 | 5/1990 | Lott et al. | 128/155 |
| 5,012,801 | 5/1991 | Feret | 128/155 |
| 5,018,515 | 5/1991 | Gilman | 128/155 |
| 5,035,687 | 7/1991 | Sandbank | 604/180 |
| 5,042,466 | 8/1991 | McKnight | 128/155 |
| 5,074,293 | 12/1991 | Lott et al. | 128/155 |
| 5,088,483 | 2/1992 | Heinecke | 602/46 |
| 5,092,323 | 3/1992 | Riedel et al. | 602/54 |
| 5,106,629 | 4/1992 | Cartmell et al. | 424/445 |
| 5,158,555 | 10/1992 | Porzilli | 604/307 |
| 5,204,110 | 4/1993 | Cartmell et al. | 424/443 |
| 5,225,199 | 7/1993 | Hidaka et al. | 424/443 |

FOREIGN PATENT DOCUMENTS

| | | | |
|---|---|---|---|
| 3809539A1 | 6/1989 | Germany | A61F 13/02 |
| 2192792 | 1/1988 | United Kingdom | A61F 13/02 |

OTHER PUBLICATIONS

I. Kelman Cohen, et al., *Wound Healing, Biochemical & Clinical Aspects*, W. B. Saunders Company, Harcourt Brace Jovanovich, Inc., Library of Congress Cataloging–in–Publication Data, 1992, pp. 562–580.

Bertek Intergrated Pouch/Patch Delivery Systems, 1990, Bertek, Inc. (6 pages).

Primary Examiner—Chester T. Barry
Attorney, Agent, or Firm—Vinson & Elkins

[57] ABSTRACT

A wound dressing delivery system is disclosed that includes a film which is to be applied to a patient's wound; a protective cover, which is adjacent to the film; an adhesive layer on one surface of the film; a tab located to one end of the adhesive layer; a release liner covering the adhesive layer and tab; and a tape which is used to connect the release liner with the protective cover. Additionally, a method of manufacturing a wound dressing delivery system is disclosed. The method of manufacturing includes the steps of casting a film onto a protective cover, coating the film with an adhesive layer, placing a tab on one end of the adhesive layer, placing a release liner over the adhesive layer, and connecting the release liner and the protective cover with a tape.

15 Claims, 5 Drawing Sheets

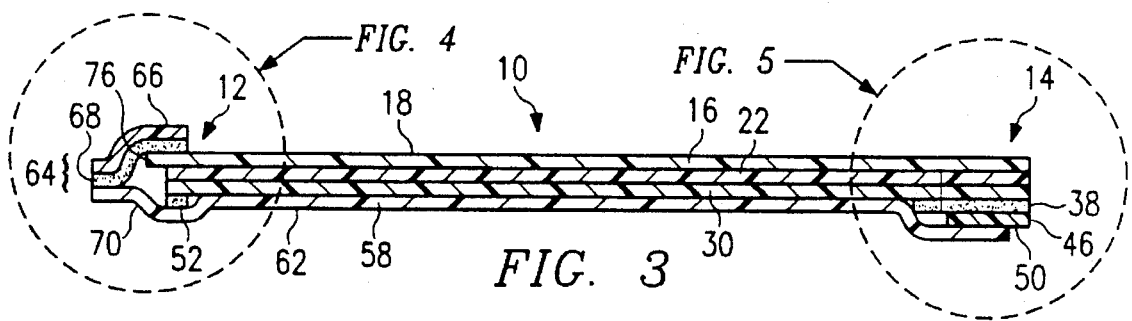
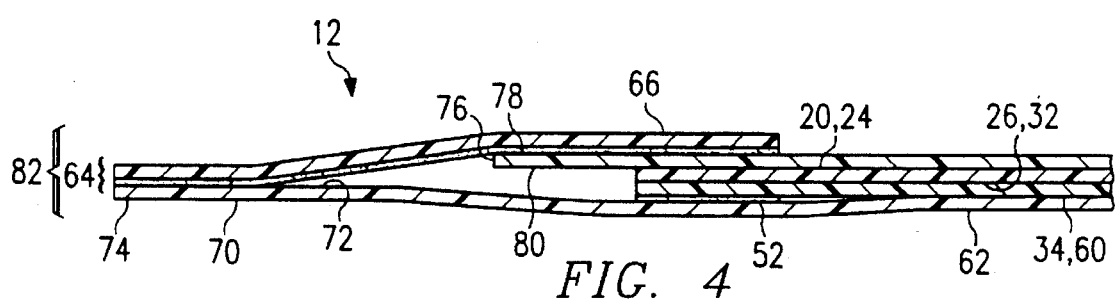
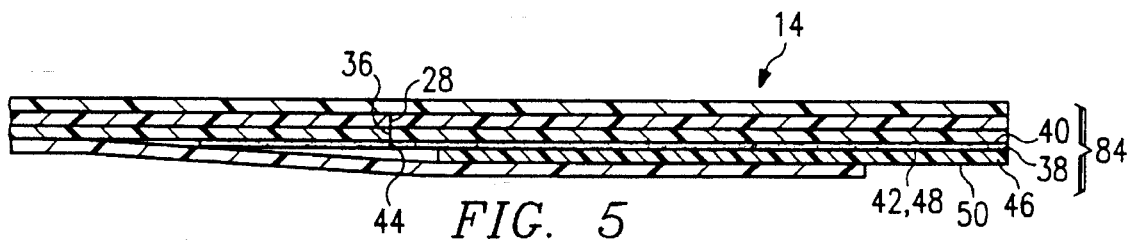
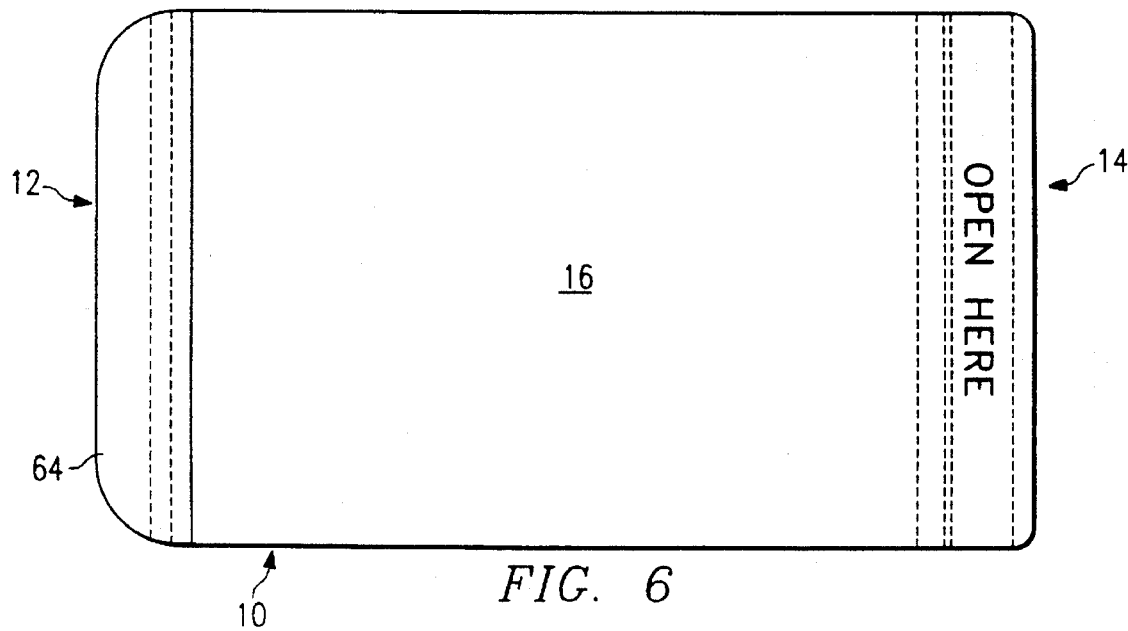

METHOD OF MANUFUCTURING A WOUND DRESSING DELIVERY SYSTEM

RELATED APPLICATION

This application is related to co-pending patent application Ser. No. 08/173,758 filed Dec. 23, 1993, of same assignee (Attorney's Docket 20064-0111), now U.S. Pat. No. 5,415,627.

TECHNICAL FIELD OF THE INVENTION

The invention relates to wound dressings, and more particularly to an improved wound dressing delivery system and an improved method of manufacturing a wound dressing delivery system.

BACKGROUND OF THE INVENTION

A wound dressing is a material applied to a wound or a diseased part of the body, with or without medication, to protect and assist healing. The treatment and the healing of wounds is an art old as humanity. There are, for example, accounts of Egyptians using honey as a dressing for use in wound care management dating back to 3,000 to 2,500 B.C. The techniques and understanding of wound treatment have continued to develop since that time, and in the last decade, the understanding and treatment of wounds has significantly improved due to studies at the molecular level and due to newly developed wound care products. See generally, I. Kelman Cohen, Robert F. Diegelmann, and William J. Lindblad, *Wound Healing: Biochemical and Clinical Aspects* (1992).

A simplified model of wound healing may involve three basic stages. First, acute inflammatory events occur which limit damage and clear the stage for subsequent repair to take place. Second, formation of fibrovascular granulation tissue and the epithelialization occur. Third, remodeling and maturization of scar tissue occurs. In this process, wound dressings may be an important part of the wound treatment in helping to isolate the wound from the harmful external environment as desired, in performing a hemostasis function, and in helping to prevent wound infection. While a dressing cannot sterilize a wound, it may create a condition for reducing the pathogenic load by preventing overgrowth and colonization or by delivering antimicrobial agents to the wound. See Id.

In using wound dressings as a part of a wound care treatment strategy, it may be desirable in some situations to frequently change the wound dressing. Because of frequent changes of the dressings, it may be desirable to have wound dressings that are both easily administered and inexpensive. In this regard, a number of devices have appeared in the wound dressing art.

Wound dressings known in the art have not, however, provided a wound dressing or dressing delivery system that is sufficiently easy to manufacture so as to provide a relatively inexpensive dressing or delivery system. Furthermore, the wound dressings known in the art have generally been difficult to administer—at least as to wound dressings having a dressing or delivery system involving thin films. While some improvement has been made in the delivery systems for such dressings, there have been shortcomings in the designs. Prior art designs have generally called for complicated manufacturing techniques, or design features that require complicated manufacturing techniques to produce, and have frequently required the use of additional adhesive layers. This latter shortcoming, increases the chance that the health care provider will inadvertently make contact with the additional adhesive layers. Additionally, some research has suggested the importance of oxygen in wound healing, and an additional adhesive layer may adversely affect the oxygen permeability as well as the moisture vapor transmission rate (MVTR) of the film.

Thus, a need has arisen for a dressing and dressing delivery system that is easily administered to a patient's wound while requiring a minimal number of adhesive layers and being relatively easy and inexpensive to manufacture.

SUMMARY OF THE INVENTION

In accordance with the present invention, a wound dressing delivery system and a method of manufacturing a wound dressing delivery system are provided that substantially eliminate or reduce the disadvantages and shortcomings associated with the prior wound dressing delivery systems and methods.

According to one aspect of the present invention, a wound dressing delivery system is provided including a film, a protective cover, which is temporarily attached to the film without requiring an adhesive therebetween, an adhesive layer attached to the film, a tab on one end of the adhesive layer, a release liner covering the adhesive layer, and tape overlying and connecting a portion of the release liner and protective cover.

According to another aspect of the present invention, a method of manufacturing a wound dressing delivery system is disclosed that includes applying a film onto a protective cover in manner that creates a temporary bond therebetween, coating the film with an adhesive layer, placing a tab on one end of the adhesive layer, placing a release liner on the adhesive layer and securing the release liner and the protective cover on one end with tape.

A technical advantage of the present invention is that it provides a delivery system that is relatively easy to manufacture, and thus having a reduced expense associated with its manufacture. Yet another technical advantage of the present invention is that only one adhesive layer is required for the dressing delivery system, which may decrease the likelihood of inadvertent contact with an adhesive and may allow for greater oxygen permeability and a higher moisture vapor transmission rate.

BRIEF DESCRIPTION OF THE DRAWINGS

For a more complete understanding of the present invention, and the advantages thereof, reference is now made to the following descriptions taken in conjunction with the accompanying drawings, in which:

FIG. 3 is a schematic view in cross section of the wound dressing delivery system of FIGS. 1 and 2;

FIG. 4 is a schematic view in cross section of the pivot end 12 of the system 10 of FIG. 3;

FIG. 5 is a schematic view in cross section of the opening end 14 of the system 10 of FIG. 3;

FIG. 6 is a plan view of the wound dressing system of FIGS. 1 through 5;

DETAILED DESCRIPTION OF THE INVENTION

The preferred embodiment of the present invention and its advantages are best understood by referring to FIGS. 1–13 of the drawings, like numerals being used for like and corresponding parts of the various drawings.

Figure 1:
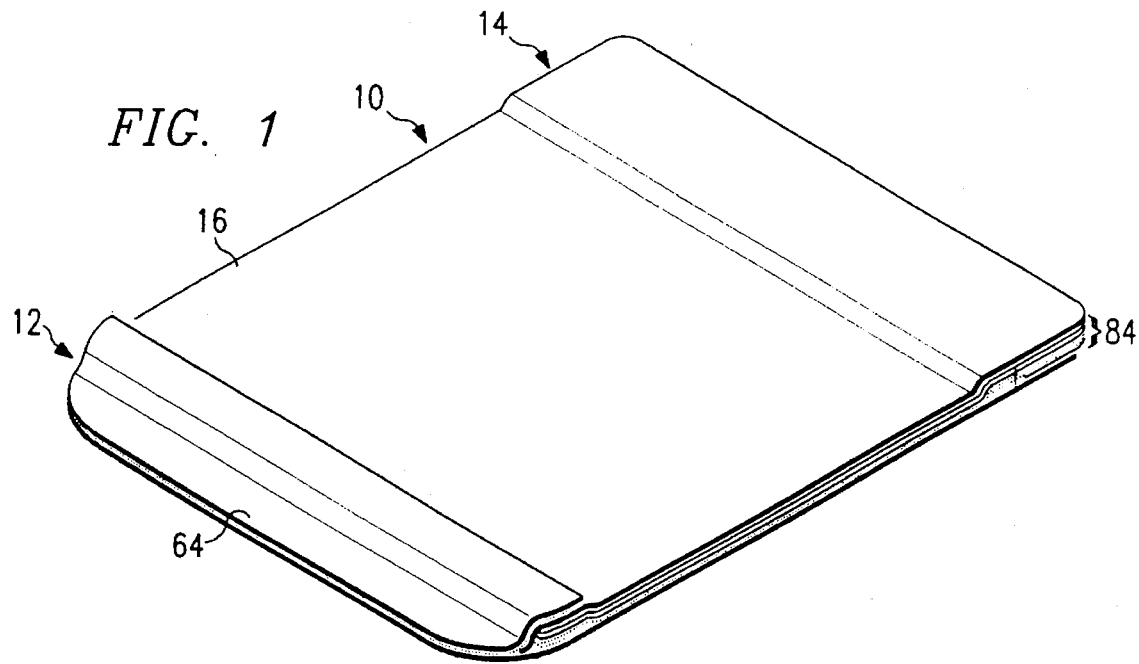
FIG. 1 is a schematic isometric view of a wound dressing delivery system according to one aspect of the present invention.
Figure 2:
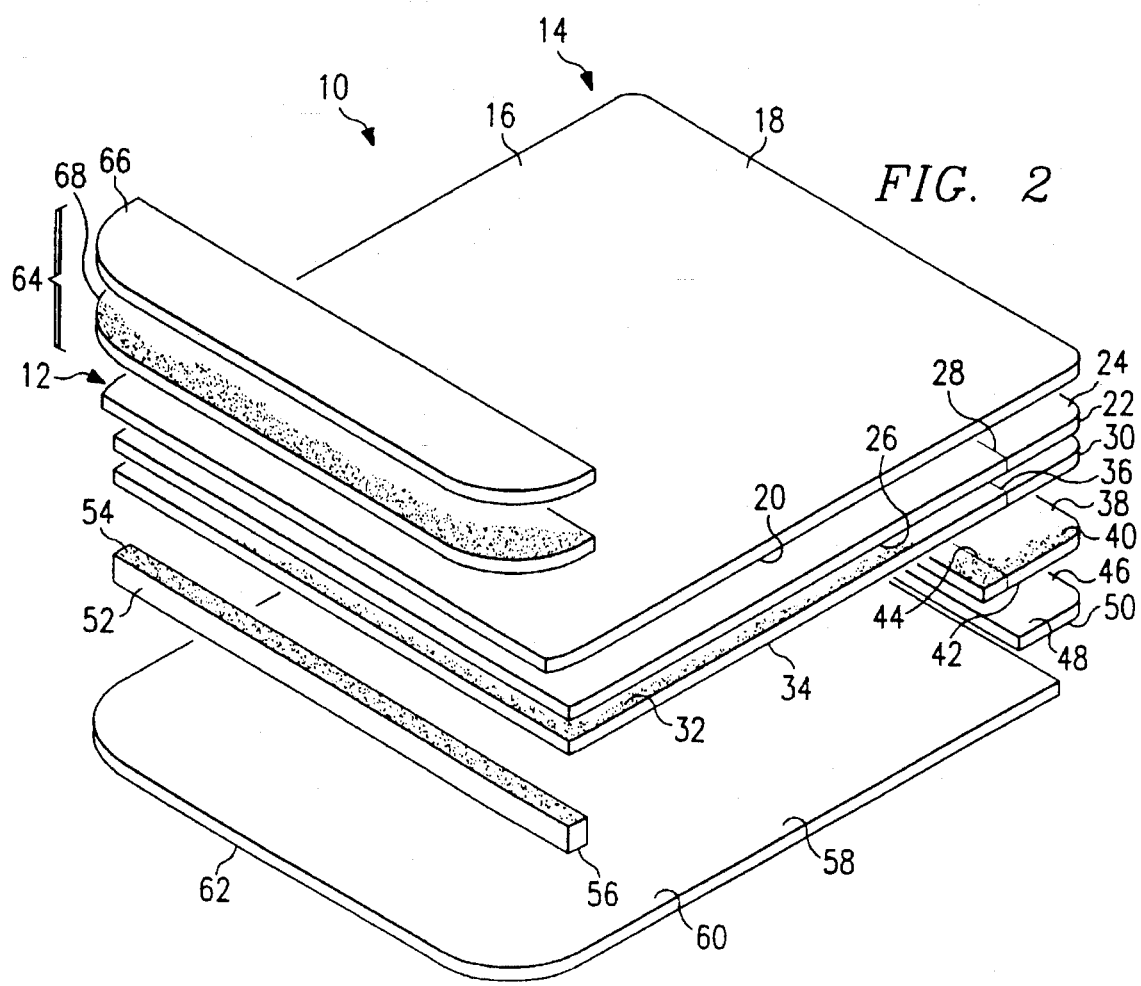
FIG. 2 is a schematic isometric exploded view of the wound dressing of FIG. 1.

Referring to FIG. 1, wound dressing delivery system 10 is shown with the components, which will be described below, shown with exaggerated thicknesses and not to scale. Wound dressing delivery system 10 has a pivot end 12 and an opening end 14.

Referring to FIGS. 1 through 6, wound dressing delivery system 10, shown with exaggerated thicknesses, may be seen. Wound dressing delivery system 10 is shown with a protective cover 16 having a first side 18 and a second side 20. A film 22 is adjacent protective cover 16. Film 22 has a first side 24 and a second side 26. A kisscut 28 is formed through a portion of film 22 proximate opening end 14. An adhesive layer 30 having a first side 32 and a second side 34 may be adjacent film 22. A kisscut 36 is made through adhesive layer 30 proximate opening end 14. A first adhesive strip 38 is shown adjacent adhesive layer 30 and proximate opening end 14. Adhesive strip 38 has a first side 40 and a second side 42. A kisscut 44 is formed through one end of adhesive strip 38. Adjacent to adhesive strip 38 is tab 46. Tab 46 has a first side 48 and a second side 50. Adjacent adhesive layer 30 near pivot end 12 is a second adhesive strip 52, which has a first side 54 and a second side 56. Adjacent to second adhesive strip 52, tab 46, and adhesive layer 30 is release liner 58. Release liner 58 has a first side 60 and a second side 62. Tape 64 is located on pivot end 12 and has a backing material 66 and a tape adhesive 68.

FIG. 3 shows a cross section of the components comprising one embodiment of the wound dressing delivery system 10, and FIGS. 4 and 5 show pivot end 12 and opening end 14 respectively in cross section. Release liner 58 extends past the pivot end or termination edge of adhesive layer 30, film 22, and protective cover 16 to form a release liner extension 70 having a first side 72 and a second side 74. A portion of protective cover 16 extends past the pivot end or termination edge of film 22 and adhesive layer 30 to form a protective cover overhang 76, which has a first side 78 and a second side 80. Protective cover overhang 76 may prevent migration of adhesive 68 of tape 64 into contact with adhesive layer 30 near pivot end 12, which might interfere with the proper application of a wound dressing with system 10.

A pivot assembly 82 (FIG. 4) is formed by tape 64, release liner overhang 70, a portion of protective cover 16 proximate pivot end 12, a portion of film 22 proximate pivot end 12, a portion of adhesive layer 30 proximate pivot end 12, and in some embodiments, as will be discussed below, second adhesive strip 52. Pivot assembly 82 connects protective cover 16 and release liner 58 in a manner that greatly simplifies the manufacturing process of system 10 while allowing simplified application of a wound dressing to a patient.

In a preferred embodiment, protective cover 16 may be a polyester material with a silicone coating on second side 20. The silicone coating which is applied to second side 20 of protective cover 16 allows film 22 to be solvent casted onto side 20 of protective cover 16. In a solvent casting process, the material is poured onto the casting sheet or protective cover 16 and heated in an oven and then the solvent is driven off; the remaining materials or solids solidify to form the appropriate substrate. The casting of film 22 onto second side 20 of protective cover 16 creates a temporary and releasable bond that provides a means for temporarily attaching second side 20 to first side 24 of film 22.

The temporary attachment is by the cohesive interaction of film 22 and protective cover 16. The ability to releasably and temporarily attach film 22 onto protective cover 16 without requiring adhesives is an important aspect of the present invention. While the preferred embodiment creates the temporary attachment of film 22 and protective cover 16 by solvent casting film 22 onto cover 16, it is to be understood that the temporary attachment may be achieved by other techniques such as extruding film 22 onto cover 16.

Protective cover 16 may be formed of any material which is suitable for use with the technique used to create the temporary and releasable bond to be produced between protective cover 16 and film 22, e.g., protective cover suitable for use with solvent casting for the preferred embodiment. A polyester material is used in the preferred embodiment for cover 16. Other suitable materials for protective cover 16 include polypropylene with a silicone coated release material or any substrate that is coated or provided to allow the temporary and releasable bond to be created and that improves the release of the material from that substrate. Another example of a suitable material for cover 16 is kraft paper with or without a silicone coating.

Adhesive layer 30 is preferably a modified acrylic adhesive that is pressure sensitive. There are, however, a plethora of adhesives that may be used as part of the present invention. Other adhesives that may be appropriate include water activated adhesives (hydroactive), hydrophobic adhesives, hydrophilic adhesives, pressure sensitive adhesives or non-pressure sensitive adhesives. Acrylic- or silicone-based, or rubber-based adhesives or modified-acrylic-based adhesives may be used. Additionally, active adhesives may be used, which include various drug or chemical components mixed with the adhesive; for example, growth factors may be included in the adhesive such as epidermal growth factor (E.G.F.), fibroblast growth factor (F.G.F.), platelet-derived growth factor (P.D.G.F.) and transforming growth factor—$\beta$ (T.G.F.—$\beta$). Adhesive layer 30 may also include a medicated ingredient such as an antimicrobial. Adhesive layer 30 may be continuous or discontinuous. The latter coverage is utilized in the preferred embodiment for adhesive layer 30. Forming adhesive layer 30 as a discontinuous layer may increase oxygen permeability and moisture vapor transmission rate of the dressing.

Tape or splice tape 64 is preferably a silicone tape. Different tapes may, however, be used. An alternative tape may be desirable for different release liners 58. As will be described more fully below, tape 64 is placed over release liner overhang 70 and protective cover overhang 76 to connect overhangs 70 and 76 in a manner that may be easily executed during the manufacturing process. As shown in FIG. 3, release liner overhang 70 may extend beyond protective cover overhang 76 with tape 64 connecting overhangs 70 and 76 from the top for the orientation shown in FIG. 3. An alternative embodiment of this aspect of pivot assembly 82 is utilized in the embodiment shown in FIG. 8.

Figure 8:
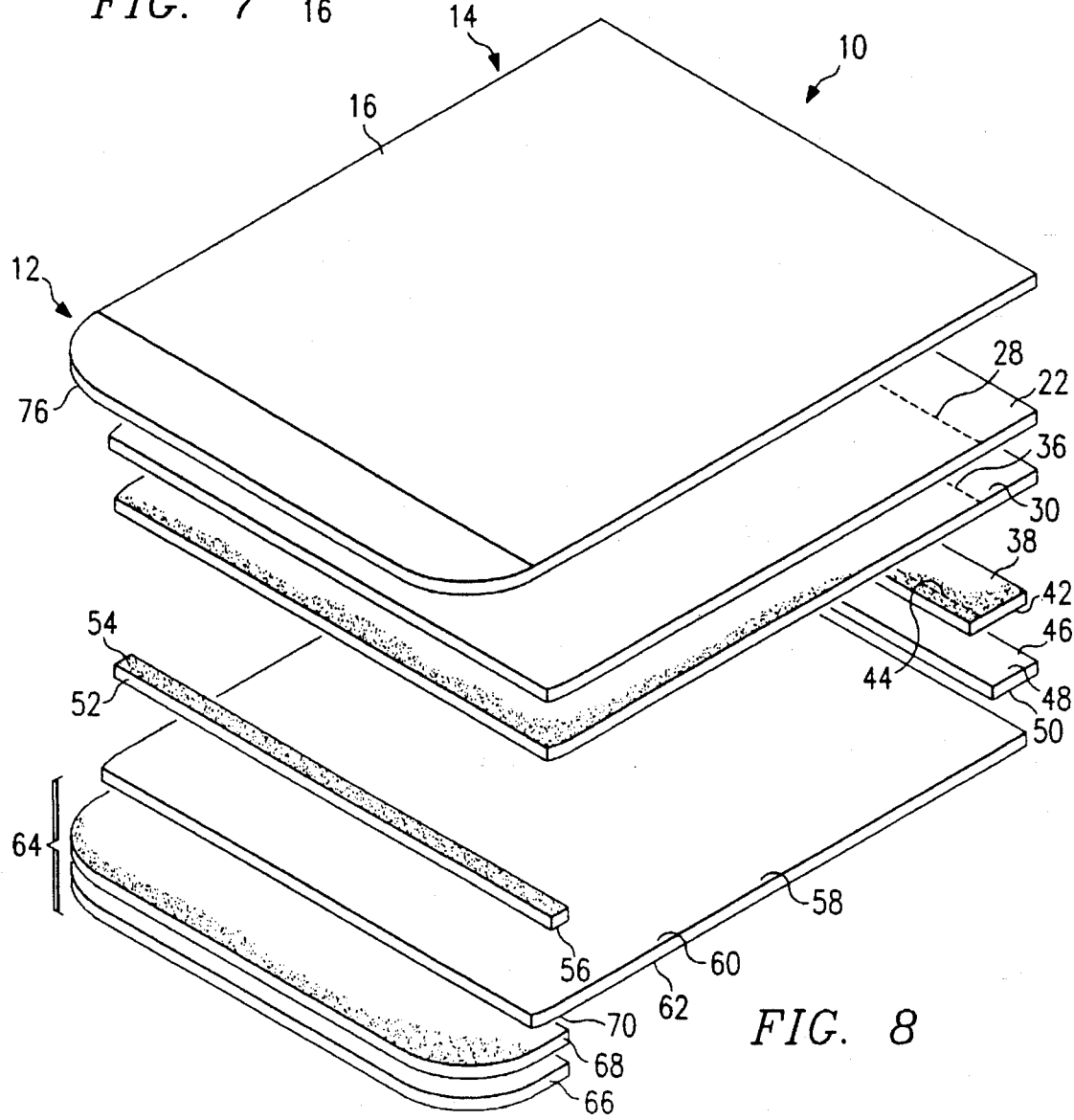
FIG. 8 is a schematic isometric exploded view of a third embodiment of a wound dressing delivery system according to the present invention.

In the embodiment of FIG. 8, protective cover overhang 76 extends beyond release liner overhang 70 so that tape 64 may be applied from a direction opposite to that of the embodiment of FIGS. 1 through 6, i.e., from the bottom for the orientation shown in FIG. 8. Yet another alternative for securing protective cover 16 and release liner 58, is to make protective cover overhang 76 and release liner overhang 70 approximately the same length, and then to wrap tape 64 around the resultant edge so that a portion of tape adhesive 68 is in contact with first side 78 of protective cover overhang 76 and a portion of second side 74 of release liner overhang 70.

The relative strengths of the cohesive forces involved in system 10 are an important aspect of the present invention. In applying wound dressing delivery system 10, it is necessary that the cohesive interaction between protective cover 16 and film 22 resulting from the temporary and releasable bond have a smaller cohesive force than is developed between adhesive layer 30 and a patient's wound or flesh. Because the cohesive force between adhesive layer 30 and the patient is greater than the cohesive force developed by film 22 and protective cover 16, as protective cover 16 is pulled away from the patient, protective cover 16 will release or separate from film 22 before adhesive layer 30 releases from the patient's wound or skin. Additionally, the cohesive force developed between adhesive layer 30 and second side 26 of film 22 must likewise be greater than the cohesive force developed by film 22 and protective cover 16.

One means of assuring that the cohesive force between adhesive layer 30 and the patient's wound or skin is greater than the other mentioned cohesive forces, is to provide additional adhesive strips 38 and 52 onto adhesive layer 30; these strips 38 and 52 will increase the cohesive force between adhesive layer 30 and the skin or wound. Adhesive strips 38 and 52 may be formed of the same adhesive material from which adhesive layer 30 is formed.

In an alternative embodiment, adhesive strips 38 and 52 are not required, but an adhesive, which forms adhesive layer 30, is used that develops a cohesive force that is greater than the cohesion force of the releasable bond between protective cover 16 and film 22.

Tab 46 facilitates application of system 10 to a patient and provides a barrier to prevent the physician or medical care provider's hand from coming into contact with the adhesive of adhesive layer 30. When tab 46 is pulled away from a portion of release liner 58 proximate opening end 14, a force may be developed that pulls release liner 58 away from adhesive layer 30 to allow adhesive layer 30 to be exposed for application to the patient. See FIG. 9. As shown clearly in FIGS. 3 and 5, tab 46 may be placed over first adhesive strip 38, but adhesive strip 38 extends beyond an end of tab 46, which is opposite the extreme opening end 14 of tab 46. The portion of adhesive strip 46 that extends past tab 46 and is on the pivot end 12 side of kisscut 36, is the portion of first adhesive strip 46 that provides additional adhesive force between adhesive layer 30 and the patient as described above. Tab 46 may be any non-releasable or release-resistant material, but is preferably a paper strip.

Figure 9:
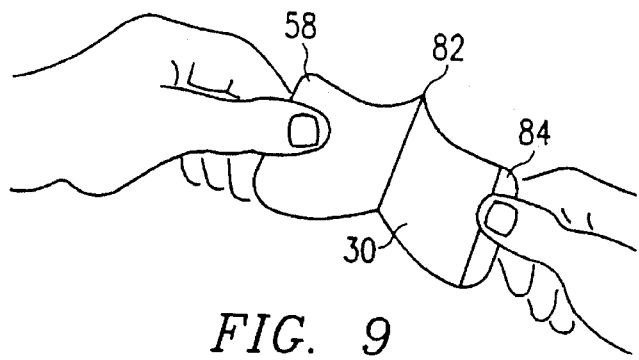
FIG. 9 is a schematic of the wound dressing delivery system of FIGS. 1–6 showing the removal of the release liner from the adhesive layer.
Figure 10:
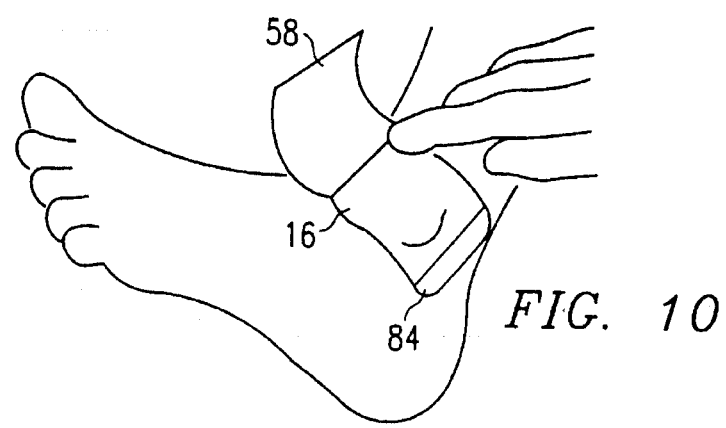
FIG. 10 is a schematic view of the wound dressing delivery system of FIGS. 1–6 showing the application of the adhesive layer and the film to the wound of a patient.
Figure 12:
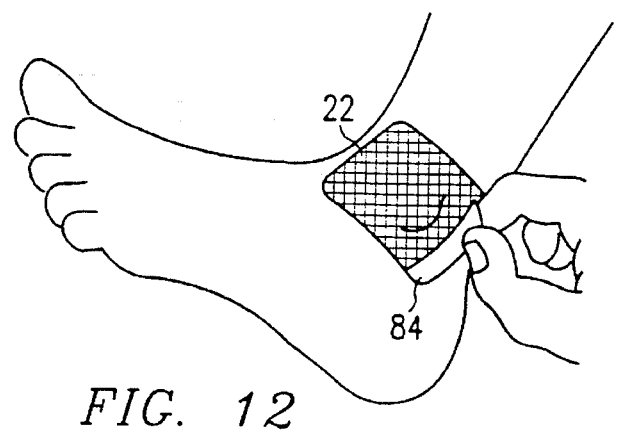
FIG. 12 is a schematic view of the wound dressing delivery system of FIGS. 1–6 showing removal of the tab from the film.

Referring to FIG. 5, a handle assembly 84 is formed by tab 46, a portion of first adhesive strip 38, a portion of adhesive layer 30 proximate opening end 14, and a portion of film 22 proximate opening end 14. Handle assembly 84, in conjunction with pivot assembly 82, greatly facilitates the application of film 22 to a wound or the skin of a patient. Handle assembly 84 may be gripped or held by one hand of the physician or health care provider while the other hand is used to pull and hold liner 58 to facilitate applying adhesive layer 30 to the patient's wound or skin as shown in FIGS. 9–10. Handle assembly 84 may be removed from system 10 after application of film 22 to the patient as shown in FIG. 12.

For the purpose of removing handle assembly 84, kisscuts 28, 36, 44 may be placed through portions of handle assembly 84. Film 22 has kisscut 28. Adhesive layer 30 has kisscut 36. First adhesive strip 38 has kisscut 44. Kisscuts 28, 36, and 44 allow handle assembly 82 to be removed from other portions of system 10 after protective cover 16 is removed as shown in FIG. 12.

Yet another important aspect of system 10 is kisscut 44 through first adhesive strip 38. The portions of adhesive strip 38 adjacent to and along each side of kisscut 44 migrate on to each other and provide an adhesive force between adhesive layer 30 and tab 46. When the health care provider is preparing system 10 for application, the health care provider pulls release liner 58 away from handle assembly 84 as shown in FIG. 9, and this causes the cohesive force developed in first adhesive strip 38 adjacent kisscut 44 to allow a force to be developed on side 26 of film 22 which facilitates removal of layer 30 from release liner 58 without causing or tending to cause cover 16 to separate from film 22.

Release liner 58 may be any suitable release means for covering adhesive layer 30 and protecting adhesive layer 30 from contaminates and allowing development of a cohesive force between adhesive layer 30 and liner 58 that is smaller than the cohesive force between adhesive layer 30 and film 22 and between film 22 and protective cover 16. The cohesive force between adhesive layer 30 and release liner 58 may be the smallest of the cohesive forces in system 10. If an active ingredient is included with adhesive layer 30, release liner 58 should be appropriately selected to act as a barrier to the active ingredient. In the preferred embodiment, a paper with a silicone coating on first side 60 is utilized for release liner 58.

Film 22 (and possibly additional substances as discussed below) with adhesive layer 30 on second side 26 of film 22 is the wound dressing that remains on the patient as a final result of using wound dressing delivery system 10. In the preferred embodiment, film 22 is a polyurethane film that is 50–55 microns in thickness, but numerous films may be used for film 22 according to the desired treatment of the patient's wound. For example, polypropylene may also be used for film 22. Film 22 may have different characteristics according to its intended use; for example, film 22 may be permeable, impermeable, semi-impermeable, or occlusive, non-occlusive, or semi-occlusive. The material of film 22 may be a woven, non-woven, or knitted material. Film 22 may be any thin suitable material such as polyurethane, polypropylene, hydrocolloids with or without active ingredients such as growth factors or components such as calcium, sodium, chitin, zinc, or derivatives thereof, and/or various alginates, whether natural or synthetic. Additionally, film 22 may include or be formed as hydrated or dehydrated hydrogels which may include the active ingredients and components described above for the hydrocolloids. Film 22 may be, and is in the preferred embodiment, transparent to allow for viewing of the patient's wound during the application of the dressing to the wound, or to view the wound after the dressing has been applied.

Figure 7:
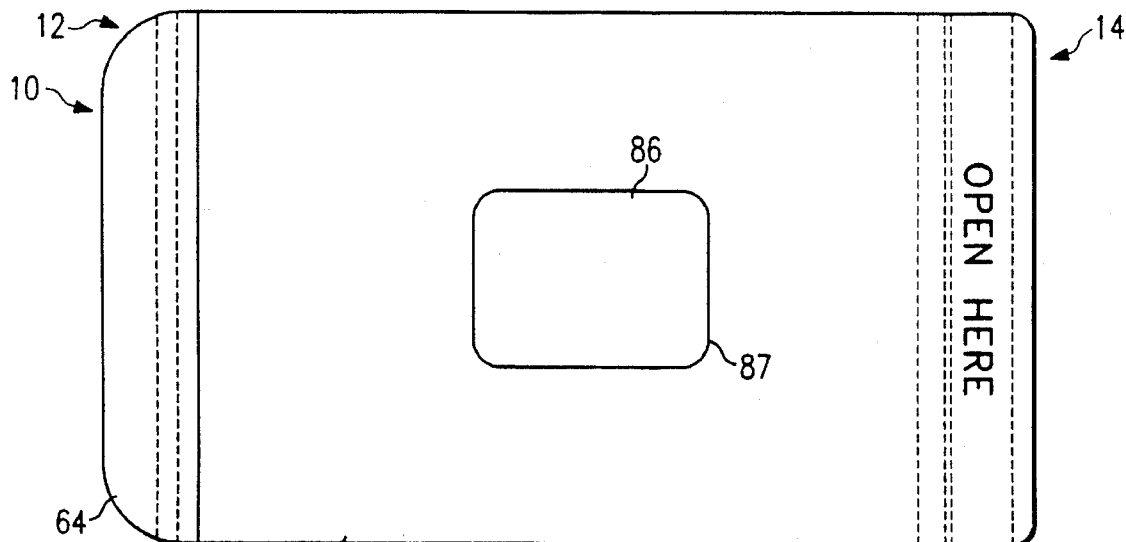
FIG. 7 is a plan view of a second embodiment of a wound dressing delivery system according to the present invention showing a substance-containing island.

As shown in FIG. 7, a substance-containing island 86 may be incorporated as part of delivery system 10. Substance-containing island 86 may contain, for example, a hydrocolloid material, a hydrogel, an active ingredient, or other substances. Hydrocolloid material which may be contained within substance-containing island 86 may be with or without active ingredients such as growth factors or components such as calcium, sodium, chitin, zinc, or derivatives, and/or various alginates, whether natural or synthetic. Similarly, a hydrogel may be contained within the substance-containing island 86; the hydrogel may be hydrated or dehydrated and may be with growth factors or components such as calcium, sodium, chitin, zinc, or other derivatives, and/or various alginates, whether natural or synthetic.

Substance-containing island 86 may be formed by placing the desired substance onto adhesive layer 30 prior to applying release liner 58. Alternatively, the substance of substance-containing island 86 may be placed against adhesive layer 30 and then covered by a membrane. The membrane may be selected to control the rate at which an active ingredient permeates the membrane and is thus the rate at which the active ingredient is administered to the wound or skin of the patient. Substance-containing island 86 may have perforations or a kisscut about its border 87 to allow application of the substance-containing island 86 with system 10 and then removal of the surrounding film 22. Substance-containing island 86 is shown in FIG. 7 centered relative to film 22, but it is to be understood that substance-containing island 86 may take any shape and may be located anywhere on film 22. In this regard, although system 10 is generally shown in the figures as rectangular, it is to be understood that wound dressing delivery system 10 may be formed in any geometric shape.

Referring to FIGS. 9 through 12, the application of the first embodiment (FIGS. 1–6) of the wound dressing delivery system 10 of the present invention is shown being applied to a patient. Referring to FIG. 9, the health care provider holds a portion of release liner 58 that overhangs or is adjacent to tab 46 on opening end 14, and grabs tab 46 of handle assembly 84 and pulls the two apart. This pulling action causes release liner 58 to be removed from adhesive layer 30, while maintaining the other layers 30, 22 and 16 as they were because of the relative strength of the cohesive forces previously discussed. Release liner 58 is pulled until it reaches pivot assembly 82 so that adhesive layer 30 is exposed.

Referring to FIG. 10, the now exposed adhesive layer 30 is placed over the portion of the patient's body to be covered by the dressing (film 22 and adhesive layer 30 and any substance in substance-containing island 86, if any). Pressure may then be applied by the health care provider to first surface 18 of protective cover 16 along the edges thereof to allow adhesive layer 30 to make good contact with the patient.

Figure 11:
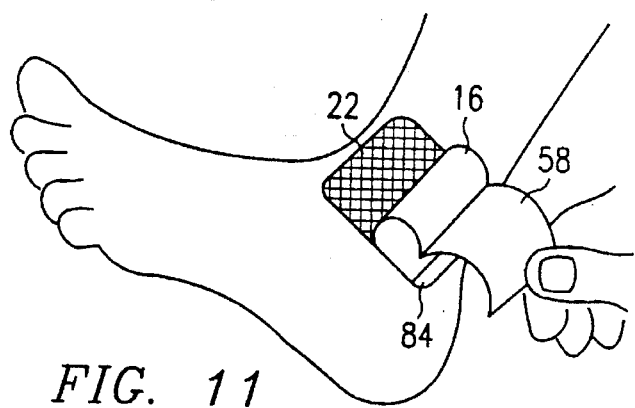
FIG. 11 is a schematic view of the dressing delivery system of FIGS. 1–6 showing the removal of the protective cover from the film of the delivery system.

Referring to FIG. 11, the health care provider may then to pull release liner 58 away from the patient as shown which causes the releasable bond between film 22 and protective cover 16 to be severed or released because of the relative strength of the cohesive forces as previously described. The health care provider continues to pull liner 58 until release liner 58 and protective cover 16 are completely removed from film 22.

Then, as shown in FIG. 12, handle assembly 84 may be easily removed from the remaining portion of film 22 and adhesive layer 30 because of kisscuts 28, 36, and 44 through the portions of handle assembly 84. The health care provider removes handle 84 by pulling on handle 84 away from film 22; this pulling by the health care provider creates a force on handle 84 away from film 22 which separates handle 84 from film 22, adhesive layer 30, and first adhesive strip 38 along kisscuts 28, 36 and 44. Thus, the dressing is easily administered to the patient by wound dressing delivery system 10, which is easily manufactured.

The ease with which the present system may be manufactured compared to systems previously known is one of the major advantages of the wound dressing delivery system 10 of the present invention. In manufacturing the wound dressing delivery system 10 of the present invention, one step is to develop a temporary and releasable bond between film 22 and protective cover 16. In the preferred method of manufacturing system 10, the releasable bond is created by solvent casting film 22 onto protective cover 16. Film 22 is solvent cast onto second surface 20 of protective cover 16. The casting process creates a cohesion force between film 22 and protective cover 16 as previously discussed. The materials and structure of film 22 and protective cover 16 have previously been discussed.

Film 22 may then be coated with an adhesive to form adhesive layer 30. The nature of adhesive layer 30 has previously been discussed. After placing adhesive layer 30 on film 22, a first adhesive strip 38 may be placed on adhesive layer 30 proximate opening end 14. A tab 46 may be placed over a portion of first adhesive strip 38 opposite adhesive layer 30 to cover the extreme open end 14 portion of adhesive strip 38.

A second adhesive strip 52 may then be placed on second side 34 of adhesive layer 30 proximate pivot end 12. A release liner 58 may then be placed over adhesive layer 30, second adhesive strip 52, the uncovered portion of first adhesive strip 38, and tab 46.

Release liner 58 and protective cover 16 may be sized relative to film 22 and adhesive layer 30 to provide a protective liner overhang 70 and a protective cover overhang 76 as shown in FIG. 3. Protective liner overhang 70 is further sized to extend beyond the extreme pivot end 12 or termination edge of protective cover 16 so that a tape 64 may then be disposed or placed over overhangs 70 and 76 to connect to them. The materials and relative cohesive force developed by these components have previously been discussed.

Figure 13:
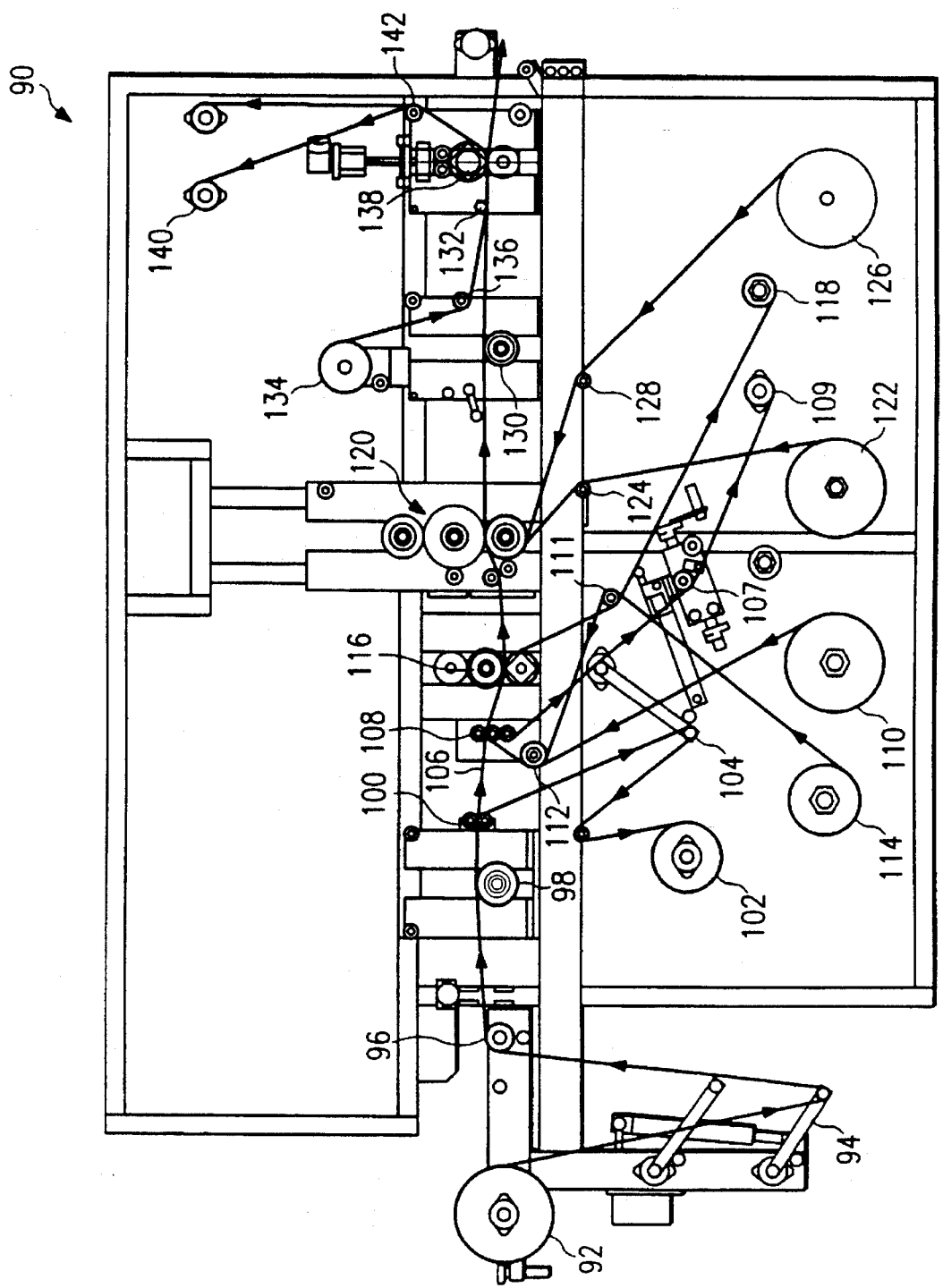
FIG. 13 is a schematic view in elevation of a general purpose rotary press configured to manufacture a wound dressing delivery system according to another aspect of the present invention.

Referring to FIG. 13, a general purpose rotary press 90 is shown as is used in a preferred method of manufacturing wound dressing delivery system 10. A roll of material with four components is loaded on spindle 92; the four components may include protective cover 16, film 22, adhesive layer 30, and a temporary liner adjacent to adhesive layer 30. The temporary liner is placed over second side 34 of adhesive layer 30 to prevent adhesive layer 30 from engaging first surface 18 of protective cover 16 in an unreleasable manner or with a cohesive force that is too great and that adversely affects manufacturing system 10. Without the temporary liner, the adhesive layer 30 would contact surface 18 of cover 16 because the material is rolled upon itself to form the roll on spindle 92. An alternative to using a temporary liner would be to place an additional release coating on first side 18 of cover 16 to allow it to be rolled.

Before the roll may be placed on spindle 92, the material (four components discussed above) on it is formed. To form the material on the roll of spindle 92, film 22 is first cast onto second side 20 of protective cover 16, and then adhesive layer 30 is disposed or placed on second side 26 of film 22, which may require the temporary release liner to be applied to second side 34 of adhesive layer 30 to allow the material to be wound upon itself to form the roll for spindle 92 without permanently adhering to itself as discussed above. Further ease of manufacture may be realized, however, by placing a second silicone coating, or other release coating, on first side 18 of protective cover 16 so that after casting and applying adhesive layer 30 to film 22, the resultant material 16, 22, 30 may be rolled without requiring a temporary release liner. This latter enhancement is possible because the cohesive force between the releasable bond temporarily attaching film 22 and protective cover 16 is greater than the cohesive force created by second side 34 of adhesive layer 30 coming into contact with coated first side 18 of protective cover 16.

After passing over tensioner 94 and rollers 96 and 98, the material from the roll on spindle 92 reaches temporary-liner-removal rollers 100, which remove the temporary liner from adhesive layer 30. The temporary liner which is now removed is then wound on temporary liner spindle 102 after it passes around tensioner 104.

After passing rollers 100, the material (film 22, adhesive layer 30), which is shown by reference numeral 106 passes to adhesive-strip-application station 108 where first adhesive strip 38 and second adhesive strip 52 are administered to adhesive layer 30. The adhesive material comprising first adhesive strip 38 is fed to adhesive-strip-applicator station 108 from spindle 110 after passing roller 112. Likewise, the material from which second adhesive strip 52 is formed is fed to adhesive-applicator station 108 from spindle 114 after passing a portion of rollers 111 and 112. A liner which covers adhesive strips 38 and 52 before they are applied to layer 30 is removed and wound onto spindle 109 after passing roller 107.

After leaving adhesive-applicator station 108, the material passes to first die cutting station 116 where the previously discussed kisscuts 28, 36, and 44 are made and a cut is made on the pivot end that cuts the second adhesive strip 52, adhesive layer 30, and film 22 so that the pivot end termination of these layers are substantially uniform or coterminous at their ends proximate pivot end 12, and the excess portions of film 22, adhesive layer 30 and second adhesive strip 52 are then wound from die cutting station 116 over roller 111 and onto spindle 118.

After leaving die cutting station 116, the material passes to tab/liner applicator station 120. At station 120, tab 46 and release liner 58 are applied to the material. The material from which tab 46 is formed is fed from spindle 122 after passing roller 124. Release liner material 58 is fed from spindle 126 to tab/liner applicator station 120 after passing roller 128. The material exiting after tab/liner applicator station 120 passes over roller 130 to tape laminator station 132, where tape 64 is applied to the protective cover overhang 76 and release liner overhang 70 as previously described to complete formation of pivot assembly 82 with the characteristics previously described. Tape 64 is fed from spindle 134 past roller 136 to tape laminator station 132.

The material that exits after tape laminator station 132 then passes to second die cutting station 138 where the desired shape of the wound dressing delivery system 10 is cut from the material. The excess portion remaining after the cutting process which occurs at second die cutting station 138 is removed to spindle 140 after passing roller 142. The now complete wound dressing delivery system 10 then exits rotary press 90, and may then be packaged for commercial sale.

Although the present invention and its advantages have been described in detail, it should be understood that various changes, substitutions and alterations can be made therein without departing from the spirit and scope of the invention as defined by the appended claims.

What is claimed is:

1. A method of manufacturing a wound dressing and delivery system, the system having an opening end and a pivot end, the method comprising the steps of:

casting a film onto a protective cover to create a first cohesion force between the film and protective cover and thereby, releasably attaching the film and the protective cover, wherein the film has a pivot end and the protective cover comprises a protective cover overhang extending beyond the pivot end of the film;

coating the film with an adhesive layer having a pivot end that is substantially coextensive with the pivot end of the film, the adhesive creating a second cohesion force between the adhesive layer and a patient's flesh when the wound dressing is applied, the first cohesion force smaller than the second cohesion force;

placing a tab on the adhesive layer proximate the opening end;

placing a release liner onto the adhesive layer to cover the adhesive layer, wherein the release liner has a pivot end comprising a release liner overhang extending beyond the pivot end of the adhesive layer; and securing the pivot end of the release liner and the pivot end of the protective cover with a tape having a tape adhesive by applying the tape adhesive to connect the release liner overhang and the protective cover overhang and such that the tape adhesive does not contact the adhesive layer coated on the film.

2. The method of manufacturing of claim 1, wherein the step of casting a film onto a protective cover comprises the step of casting a polyurethane film onto a polyester material.

3. The method of manufacturing of claim 1, further comprising sizing the protective cover so that the protective cover overhang extends beyond the pivot end of the film by a first distance; and sizing the release liner so that the release liner overhang extends beyond the pivot end of the adhesive layer by a second distance different than the first distance so that the release liner overhang is not coextensive with the protective cover overhang.

4. The method of claim 3, wherein the protective overhang is approximately ⅛ of inch.

5. The method of manufacturing of claim 1, wherein the step of coating the film with an adhesive layer comprises the step coating the film with a pressure-sensitive adhesive.

6. The method of manufacturing of claim 5, wherein the step of coating the film with a pressure-sensitive adhesive comprises the step of coating the film with a modified acrylic adhesive.

7. The method of manufacturing of claim 1, wherein the step of placing a release liner onto the adhesive layer comprises the step of placing a silicone coated paper onto the adhesive layer.

8. The method of manufacturing of claim 1, wherein the step of securing the pivot end of the release liner and the protective cover with a tape comprises the step of securing the pivot end of the release liner and the protective cover with a silicone tape.

9. A method of manufacturing a medical dressing and an accompanying delivery system, the system having an opening end and a pivot end, comprising the steps of:

casting a film onto a protective cover and thereby creating a first cohesion force between the film and protective cover;

coating the film with an adhesive layer so the adhesive layer is substantially coextensive with the film;

placing a first adhesive strip on the adhesive layer proximate the opening end;

placing a second adhesive strip on the adhesive layer proximate the pivot end;

cutting and removing a portion of the second adhesive strip, the adhesive layer, and the film to create a protective cover overhang;

attaching a tab to the first adhesive strip;

attaching a release liner to the adhesive layer and second adhesive strip with the release liner extending beyond the pivot end of the adhesive layer to create a release liner overhang;

laminating a tape over the release liner overhang and the protective cover overhang; and cutting the film, protective cover, release liner to form a predetermined shape.

10. The method of claim 9, wherein the step of casting a film onto a protective cover and thereby creating a first cohesion force between the film and protective cover comprises the step of casting a polyurethane film onto a polyester protective cover.

11. The method of claim 10, wherein the step of coating the film with an adhesive layer so the adhesive layer is substantially coextensive with the film comprises the step of coating the film with a pressure-sensitive adhesive layer.

12. The method of claim 11, wherein the step of placing a first adhesive strip on the adhesive layer proximate the opening end comprises placing a pressure-sensitive adhesive strip proximate the opening end of the adhesive layer.

13. The method of claim 12, wherein the step of attaching a tab to the first adhesive strip comprises attaching an uncoated paper to the first adhesive strip.

14. The method of claim 13, wherein the step of attaching a release liner to the adhesive layer and second adhesive strip comprises the step of attaching a silicone coated paper to the adhesive layer and second adhesive strip with the release liner extending beyond the pivot end of the adhesive layer to create a release liner overhang.

15. The method of claim 14, wherein the step of laminating a tape over the release liner overhang and the protective cover overhang comprises the step of laminating a silicone tape over the release liner overhang and the protective cover overhang.

* * * * *